United States Patent [19]
Golz et al.

[11] Patent Number: 5,074,474
[45] Date of Patent: Dec. 24, 1991

[54] METHOD AND EQUIPMENT FOR PRODUCING BIOACTIVE SUSPENSIONS

[75] Inventors: Karin Golz; Rainer Jung; Sebastian Kaehler; Frank Raddatz; Wilhelm Schelle, all of Berlin; Frank Vogel, Schwanebeck; Renate Winkler, Berlin, all of Fed. Rep. of Germany

[73] Assignee: VEB Berlin-Kosmetik, Berlin, Fed. Rep. of Germany

[21] Appl. No.: 231,736

[22] Filed: Aug. 12, 1988

[51] Int. Cl.$^5$ .................. B02C 19/12; B02C 19/18
[52] U.S. Cl. ................................. 241/1; 241/2; 241/30
[58] Field of Search ............. 241/1, 22, 30, 2; 366/116, 117, 127

[56] References Cited

U.S. PATENT DOCUMENTS

| | | | |
|---|---|---|---|
| 2,337,569 | 12/1943 | Pietschack | 241/1 X |
| 2,468,515 | 4/1949 | Robinson | 241/1 X |
| 2,591,083 | 4/1952 | Maier | 241/1 X |
| 2,738,172 | 3/1956 | Spiess, Jr. et al. | 241/1 X |
| 2,907,455 | 10/1959 | Sasaki | 241/1 X |
| 3,558,066 | 1/1971 | Alliger | 241/2 |

FOREIGN PATENT DOCUMENTS

| | | |
|---|---|---|
| 713929 | 10/1941 | Fed. Rep. of Germany .......... 241/1 |
| 047883 | 5/1971 | Fed. Rep. of Germany . |
| 914434C2 | 1/1980 | Fed. Rep. of Germany . |
| 26016C2 | 5/1983 | Fed. Rep. of Germany . |
| 139093C1 | 5/1983 | Fed. Rep. of Germany . |
| 16628A5 | 12/1984 | Fed. Rep. of Germany . |
| 515231A1 | 4/1986 | Fed. Rep. of Germany . |

*Primary Examiner*—Joseph Gorski
*Attorney, Agent, or Firm*—Jordan and Hamburg

[57] ABSTRACT

Biological material is suspended in a liquid and, in the presence of reverberative bodies suspended in the suspension of biological material, subjected to ultrasound thereby to disintegrate the biological material. The disintegration is conducted in a spherical chamber at approximately the center of which is the radiating surface of a sonotrode. The diameter of the chamber is at least three times the diameter of the radiating surface and the radiating surface faces the bottom of the chamber. The suspension of the biological material is pumped upwards through the chamber.

10 Claims, 1 Drawing Sheet

METHOD AND EQUIPMENT FOR PRODUCING BIOACTIVE SUSPENSIONS

BACKGROUND OF THE INVENTION

This invention relates to particularly efficient methods for producing bioactive suspensions. Typical areas of application in biotechnological, cosmetic and pharmaceutical production, therefore, are disintegration of cells of different origin, such as yeasts, bacteria, etc., and the recovery of cell contents, such as enzymes, nucleic acids and other physiologically active materials.

Suitable methods for producing bioactive suspensions can basically be divided into conventional mechanical methods and methods in which ultrasound is employed.

Up till now, only conventional mechanical methods, which usually comprise equipment for mechanical destruction, have reached industrial importance. Such equipment includes especially ball mills, mortars and extrusion homogenizers. The method steps given in DE 3,139,093, DD 216,628 and DE 3,515,231 relate primarily to comminuting methods with ball mills, temperature regimes staggered timewise and intensive stirring, which is employed additionally.

In DE 3,226,016, an installation with an extrusion homogenizer is described, in which the cells are destroyed by a high pressure gradient and cavitation and turbulence effects in a narrow gap.

It is a fundamental disadvantage of these methods and arrangements that they are very time-consuming and that the result of the disintegration is unsatisfactory. It is also disadvantageous that, in many cases, only organic compounds, which are stable over time, can be treated. Moreover, the above-mentioned mechanical methods are very energy-intensive, are responsible for high plant and operating costs and their efficiency remains restricted to a few substances of lesser resistance.

Of the possible methods of disintegration, in which ultrasonic equipment is employed, only a few are known from the literature and the brochures of manufacturing companies, which are restricted to laboratory applications. The characterizing feature of this method is the known arrangement of an ultrasonic facility, which comprises an HF generator, an electromechanical transducer with operating tool (sonotrode) and a plurality of generally open sonication vessels, which moreover, can be cooled and to which medium can be supplied continuously.

Special sonicators (cells) are also known from DE 2,027,533 and DD 2,836,741, which sonicators are coupled directly to an electromechanical ultrasonic transducer. It is a disadvantage of these sonicators that, due to the necessary construction as a wavelength-dependent resonator element, the sonicator may not be constructed of such volume that cooling is possible.

Many sonotrode shapes, suitable for sonication, are known from the technical specifications of inventions. It is a decisive disadvantage of these methods and arrangements that the result is insufficient disintegration of not more than 60%. Such a low result is due to the fact that no means for favoring the ultrasonic effect are employed and that the necessary design dimensioning of an effective sonication volume is not taken into consideration.

It is an object of the invention to provide a method and appropriate equipment for the preparation of bioactive suspensions by means of high-power ultrasound and to achieve the best possible disintegration result at little cost.

SUMMARY OF THE INVENTION

According to the invention there is provided a method, which preferably is continuous, and corresponding equipment, with which biological material, under the action of high-power ultrasound, is activated completely and disintegrated under gentle conditions.

Pursuant to the invention, ultrasound activators are added to the suspension. The displacement volume of these ultrasound activators is not more than one sixth of the capacity of the vessel.

In their geometric dimensions, the ultrasound activators are about two orders of magnitude larger than the effective ultrasound amplitude.

Preferably, the ultrasound activators comprise reverberative material, which is largely resistant to cavitation, such as hard ceramic.

The ultrasound activators may have varied shapes. The addition of propylene glycol, in addition to the suspension liquid, as ultrasonic digestion medium is particularly suitable.

Cooling is advantageous for biological material. The preferred temperatures are between 0° and 10° C. Both measures, the addition of propylene glycol and working at low temperatures, are carried out in order to achieve an increase in the effect of the ultrasound in the vessel by an improvement in the sound conduction and an increase in the dynamic inertia of the cells.

Thus, several factors, which increase the disintegration and mixing processes per unit time, act on the bioactive substance in the vessel.

The invention is particularly effective if it is carried out as a continuous method. For this purpose, the suspension is introduced into a thick-walled, spherical flow space, the diameter of which is not larger than three times the diameter on the radiating surface of the sonotrode. The sonotrode is disposed so that the radiating surface is approximately at the center of the spherical flow space. The inlet preferably is at the bottom of the flow space and the outlet above the radiating surface of the sonotrode.

The structural dimensioning of the spherical flow space, the sonotrode radiating surface and the ultrasound activators are so designed relative to one another, that the bioactive suspension is exposed more intensively to high ultrasonic amplitudes than previously. As a consequence, only a brief, single sonication is necessary, even if the proportion of solids is increased up to 50%. The inventive method thus is significantly less time-consuming and less expensive than the known methods. Through the use of the aforementioned different factors favoring the ultrasonic effect, such as the ultrasound activators cited above, the yield is increased to about 100% and a reliable and rapid disintegration is ensured even with very resistant organic substances.

DETAILED DESCRIPTION OF PREFERRED EMBODIMENTS

Figure 1:
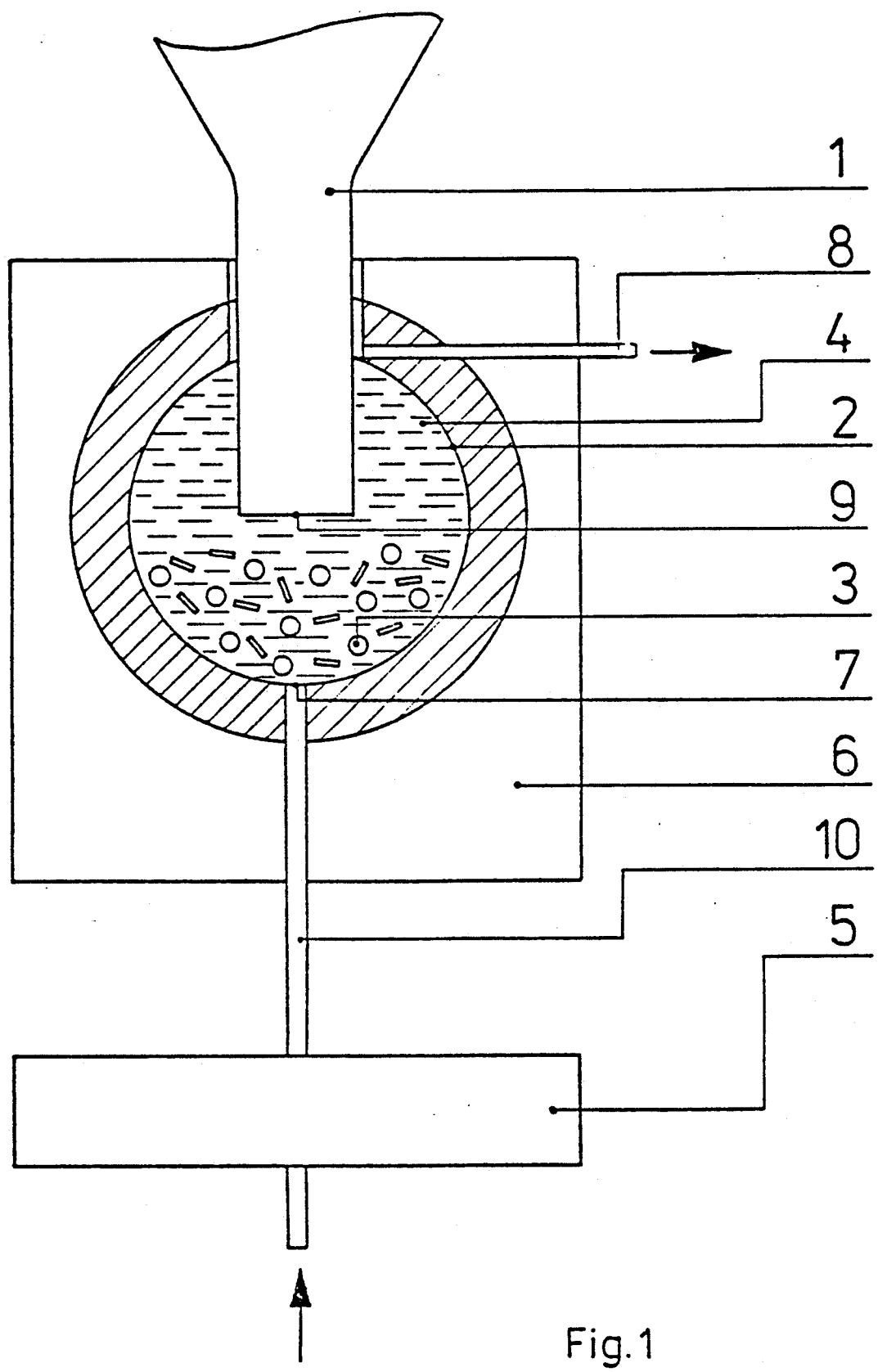

The invention will be explained in greater detail below by means of an example of the operation.

FIG. 1 is a schematic representation of apparatus according to the invention.

A high-power sonotrode 1 protrudes into a spherical flow space 2, in which, aside from the suspension 4, there are ultrasound activators 3. The suspension 4 is pumped continuously by means of pumping equipment 5 through the inlet opening 7 into the flow space 2.

The radiating surface 9 of the high-power sonotrode 1, the oscillation amplitude of which is about 50 μm, is in the center of the spherical flow space 2. The diameter of the flow space 2 is three times that of the radiating surface 9. The material and wall of the flow space are constructed technically so that sound absorption is limited to a minimum.

The ultrasound activators 3, which are also in the flow space 2 and constitute a sixth of its volume, are of importance for the method. Ultrasound activators of hard ceramic in disk shape, the diameter of which is about one hundred times the amplitude of the ultrasound, have demonstrated their value.

After being acted upon by the sound, the suspension leaves from outlet opening 8.

It is particularly advantageous to add 15% propylene glycol to the suspension and to cool the feed line 10, as well as the flow space 2, with the cooling means 6, so that the suspension 4 has a temperature of about 4° C. already on entry into the flow space 2.

We claim:

1. Method of disintegrating biological material, comprising the steps of: forming a suspension by suspending in a liquid biological material comprising cells, continuously filling to capacity a spherical chamber with the suspension and discharging the suspension from the chamber, the chamber containing ultrasound activators consisting of reverberative bodies having a displacement volume of no greater than one sixth the capacity of the chamber, and, by actuating a high power sonotrode having a radiating surface approximately at the center of the chamber, applying ultrasound of a predetermined amplitude to the suspension while the suspension is in the chamber the ultrasound activators being approximately two orders of magnitude larger than the amplitude of the ultrasound and being varied in shape.

2. Method according to claim 1, in which the ultrasound activators consist of ceramic.

3. Method according to claim 2, in which some of the ultrasound activators are discs.

4. Method according to claim 1, in which the diameter of the chamber is not greater than three times the diameter of the radiating surface of the sonotrode.

5. Method according to claim 4, comprising pumping the suspension continuously through the spherical chamber.

6. Method according to claim 5, in which the radiating surface faces the bottom of the chamber and the pumping comprises pumping the suspension into the chamber at the bottom thereof and withdrawing the suspension from the chamber at the top thereof.

7. Method according to claim 1, in which the liquid contains propylene glycol.

8. Method according to claim 1, in which the biological material consists essentially of cells.

9. Method according to claim 8, including maintaining the biological material at a temperature of between 0° and 10° C. during the application of the ultrasound.

10. Method according to claim 1, in which the sonotrode has an amplitude of oscillation of about 50 microns.

* * * * *